United States Patent [19]

Mackles

[11] 4,260,596
[45] Apr. 7, 1981

[54] EDIBLE UNIT DOSAGE FORM CONSISTING OF OUTER MANNITOL SHELL AND INNER LIQUID OR GEL CENTER AND METHOD FOR MANUFACTURING THE SAME

[75] Inventor: Leonard Mackles, New York, N.Y.

[73] Assignee: Bristol-Myers Company, New York, N.Y.

[21] Appl. No.: 66,307

[22] Filed: Aug. 13, 1979

[51] Int. Cl.³ .......... A61K 9/00; A61K 9/20; A61K 9/28; A61K 9/48

[52] U.S. Cl. .......... 424/14; 424/16; 424/35; 424/361; 426/89; 426/103; 426/548; 426/660

[58] Field of Search .......... 426/89, 103, 548, 658, 426/660; 424/14-38

[56] References Cited

U.S. PATENT DOCUMENTS

| | | | |
|---|---|---|---|
| 462,990 | 11/1891 | Oppenheimer | 424/21 |
| 943,945 | 12/1909 | Liebich | 426/103 |
| 2,531,536 | 11/1950 | Silver | 99/140 |
| 2,580,683 | 1/1952 | Kreuger | 99/165 |
| 2,770,553 | 11/1956 | Weidenheimer | 424/14 |
| 2,778,045 | 1/1957 | Bly et al. | 424/49 |
| 3,012,893 | 12/1961 | Kremzner et al. | 426/660 |
| 3,096,242 | 7/1963 | Young | 167/65 |
| 3,125,491 | 3/1964 | Elowe et al. | 167/82 |
| 3,145,146 | 8/1964 | Lieberman et al. | 167/82 |
| 3,341,415 | 9/1967 | Scott | 167/82 |
| 3,438,787 | 4/1969 | Du Ross | 426/548 |
| 3,536,074 | 10/1970 | Aufhauser | 424/37 |
| 3,556,811 | 1/1971 | Smith | 424/361 |
| 3,677,770 | 7/1972 | Witzel | 426/548 |
| 3,738,843 | 6/1973 | Frey | 426/660 |
| 3,971,852 | 7/1976 | Brenner et al. | 426/103 |
| 4,127,645 | 11/1978 | Witzel et al. | 426/548 |
| 4,156,740 | 5/1979 | Glass et al. | 426/3 |
| 4,169,885 | 10/1979 | Raaf et al. | 424/48 |

FOREIGN PATENT DOCUMENTS 1060258  3/1967  United Kingdom .......... 424/21

OTHER PUBLICATIONS

C.A. 51:2236f(1957), 58:10661e(1963), 71:21072f(1969), 74:86590e(1971), 75:101284z(1971), 76:98035(g)(1972), 81:12062g, 106678q(1974), 82:15382t 15383u, 171359w, 71833c, 77020g(1975).

Primary Examiner—Shep K. Rose
Attorney, Agent, or Firm—Irving Holtzman; George A. Mentis

[57] ABSTRACT

An edible unit dosage form comprising an outer shell made of a material containing a major portion of mannitol and a liquid or gel center which may contain a therapeutically effective amount of a medicament. The shell is sealed to the atmosphere with a suitable sealing material. Method for preparing the unit dosage form is also disclosed.

18 Claims, 6 Drawing Figures

EDIBLE UNIT DOSAGE FORM CONSISTING OF OUTER MANNITOL SHELL AND INNER LIQUID OR GEL CENTER AND METHOD FOR MANUFACTURING THE SAME

This invention relates to an edible unit dosage form capable of delivering a liquid or soft gel product. More particularly, it concerns a product of this character which comprises an edible hard outer shell covering which encompasses the liquid or soft gel center. These products can be handled and chewed so as to serve as a means for delivering a liquid or soft gelled medicament. Furthermore, the present invention is also capable of use in delivering a confection.

It is known in the prior art to provide a liquor containing confection which comprises a capsule or hollow body preferably made of sugar which contains the liquor; this capsule is also provided with an envelope or casing made of a suitable edible substance such as biscuit, cake, chocolate, or sugar. In this connection, see the U.S. Pat. No. 943,945 to Liebich granted Dec. 21, 1909.

A somewhat similar product is also disclosed in the U.S. Pat. No. 2,531,536 to Silver granted Nov. 28, 1950. The Silver patent, however, is more concerned with providing a so-called "flavor bud" comprising a hard shell and a viscous liquid flavored center. By way of example, this patent discloses a composition useful for constructing the outer shell which, among other things, contains a sizeable quantity of anhydrous dextrose and some glucose.

The U.S. Pat. No. 2,580,683 to Kreuger et al describes a capsule suitable for being filled with aqueous solutions. In this patent, the patentees disclose the inclusion of sugar in the gelatin which is employed to form the capsule.

Although there have been suggestions in the prior art of forming liquid center products encompassed by a shell comprising sugar, this has not been widely used for several reasons. In the first place, it is not possible to mold sugar conveniently into shells using the conventional molding techniques such as dip molding on a mandrel, slush molding or by standard injection molding. These techniques involve melting the molding material, shaping it while it is still in a moldable condition to the suitable form and then allowing it to cool. In the case of sugar, the molten sugar on cooling does not crystallize quickly but rather goes through an amorphous state at which time it is tacky and cannot be slushed out of the mold, for example, in the slush molding technique. Aside from this, the shells made of sugar are hydroscopic and thus have a tendency to pick up moisture from within and without the shell thereby reducing the stability and integrity of the shell.

It has now been found that the above-mentioned disadvantages can be avoided in the product of the character under consideration if mannitol is employed as the principal shell forming ingredient i.e. the mannitol comprises at least about 50% by weight and preferably from about 80% to about 100% by weight of the shell forming material. Mannitol which has a melting point of 166° C. can easily be melted and formed into various shapes and configurations. This results in shapes that are relatively strong, non-hydroscopic, sweet and are pleasant to chew. The molten mannitol quickly solidifies without residual tack and easily releases from the mold. As indicated above, this is not the case with the sugars described in the prior art.

It is accordingly an object of the present invention to provide an edible dosage form comprising a hard outer shell covering and a liquid or soft gel center which does not exhibit some of the disadvantages noted above found in similar prior art products.

It is a further object of the present invention to provide a dosage form of the above-mentioned type in which the edible outer shell comprises mannitol as a major shell forming component.

It is also an object of the present invention to provide a process for preparing the products described in the aforesaid objects.

Other and more detailed objects of this invention will be apparent from the following description, claims and drawings wherein:

As indicated above, in practicing the present invention, several procedures may be employed in forming the dosage forms of this invention. However, for the sake of convenience and ease of understanding, the so-called slush molding technique will be used to illustrate the present invention.

Figure 5:
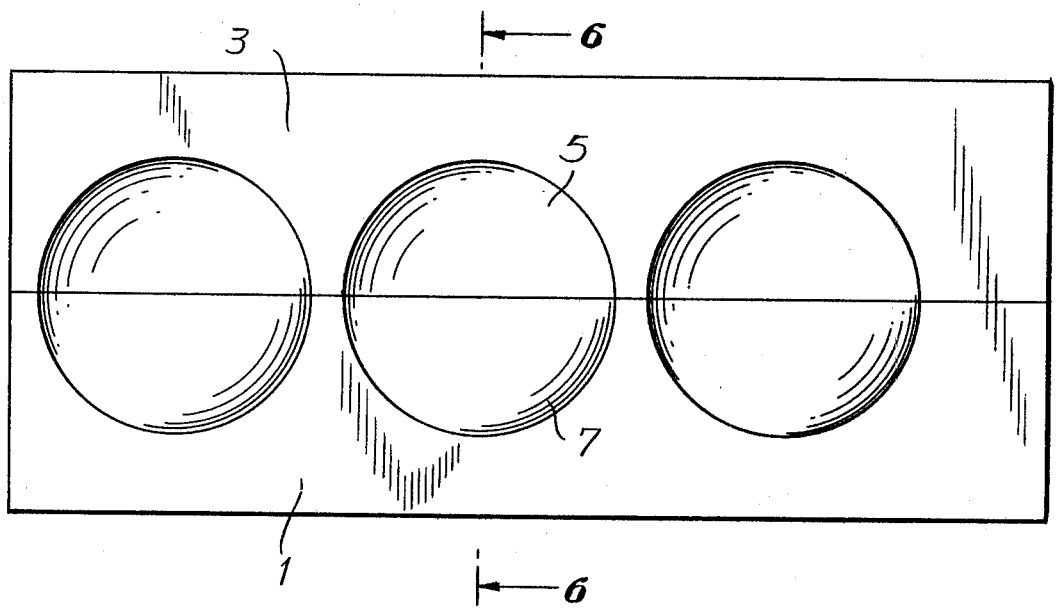
FIG. 5 is a top plan view of a mold useful in forming the shell embodied in the present invention by means of a slush molding technique.
Figure 6:
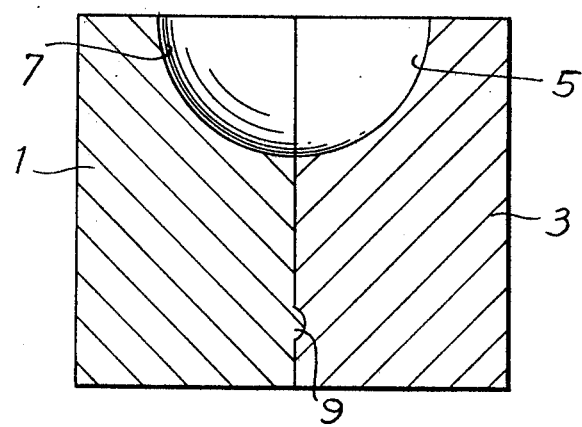
FIG. 6 is a cross section of the mold shown in FIG. 5 taken along line 5—5'.

A mold that is useful in practicing the present invention is shown in FIG. 5 of the drawings. This comprises separable mold sections 1 and 3, each of which is provided with quarter-sphere hollow cutouts 5 and 7 in their respective upper surfaces. Quarter-spheres 5 and 7 form a hemisphere when the two sections of the mold are brought together. To assure the accurate alignment of the quarter-spheres, the molds are provided with registry means as, for example, that shown at 9 in FIG. 6.

In forming the shell for the dosage forms of the present invention, molten mannitol or mannitol composition is poured into the hemispheric cavities of a chilled mold as shown in FIG. 5. The molten mannitol quickly solidifies, proceeding from the surface of the cavity mold toward the interior of the hemisphere. After a sufficiently thick wall has been formed, the remaining mannitol still in liquid or fluid form is withdrawn leaving a shaped hemisphere comprising crystalline mannitol.

The thickness of the hemisphere wall can vary somewhat depending on the results desired. Generally, this will be in the range of from about 0.5 to about 3.0 mm and preferably in the range of from about 1.0 to about 1.5 mm.

The thickness of the shell wall can be controlled by the temperature of the mold at the time the molten mannitol or mannitol composition is introduced and the time elapsed between filling the mold cavities with molten mannitol and the time that the remaining liquid or fluid mannitol is removed. Ordinarily, the temperature of the mold at the time it is filled with the molten mannitol will be in the range of from about 15 to about 30° C. The time elapsed between the filling of the mold with molten mannitol and the removal of excess fluid material will usually be in the range of from about 1 to about 5 seconds.

Figure 3:
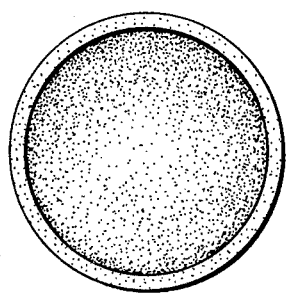
FIG. 3 is a top plan view of a shell embodied in the present invention shown before it is filled and before the top sealing lid has been applied.

The shell prepared in accordance with the process described above takes the form of a hollow hemisphere. This is shown in FIG. 3 which is a view looking into the cavity of the hemisphere. However, the present dosage form can take a variety of other suitable shapes. Thus, for example, by the appropriate mold shape unit dosage forms in the shape of hollow cylinders, hollow squares, or rectangular boxes, etc. may be made.

After the shell is made, the liquid or gel product is introduced as the center filling. Since the mannitol is water soluble, the product with which the shells are filled will ordinarily be an oil base product or a water-in-oil emulsion.

The liquid or gel centers of the unit dosage form of the present invention may contain a variety of drugs or combination of drugs. Typical among these are topical antiseptics (e.g. hexylresorcinol); topical anesthetics (e.d. benzocaine); analgesics and antipyretics (e.g. aspirin, acetaminophen); cough suppressants (e.g. dextromethorphan hydrobromide); antihistamines (e.g. chlorpheniramine maleate); pulmonary decongestants (e.g. d-pseudoephedrine hydrochloride, phenylpropanolamine hydrochloride); antacids (e.g. calcium carbonate, magnesium hydroxide, aluminum hydroxide); etc. These are employed at their therapeutically effective doses well known to those skilled in the pharmaceutical arts. Along with these active ingredients, other suitable additives may be incorporated in these liquid or gel centers. By way of illustration, mention may be made of such additives as solvents, flavoring oils, mineral and vegetable oils, emulsifiers, sweeteners, etc.

It is sometimes desirable to modify the mannitol shell for a variety of purposes such as structural, therapeutic, anesthetic or organoleptic considerations. With this in mind, such things as glycerin, sorbitol, propylene glycol, colorants, sugars, medicaments (e.g. benzocaine, hexylresorcinol), etc. may also be incorporated in the mannitol shell.

After the liquid or gel product has been introduced into the shell, it is necessary to seal off the top of the shell. It has been found in accordance with the present invention, that this may readily be accomplished by melting certain water soluble materials and pouring them into the opening in the shell. The materials that are selected for this purpose are generally floatable on the liquid or gel center material that has already been introduced into the shell. On cooling, these materials form a roof for the shell and at the same time, form a seal around its periphery with the side walls of the shell. A variety of materials are known in the prior art which may be used in this procedure. By way of example, mention might be made of Carbowax 4000 (CTFA name PEG-75), Carbowax 6000 (CTFA name PEG-150), mannitol, sorbitol and/or mixtures of these materials. Also, these materials may be mixed with glycerin, propylene glycol, butylene glycol colorants, medicaments, sugars, flavors, etc.

Figure 1:
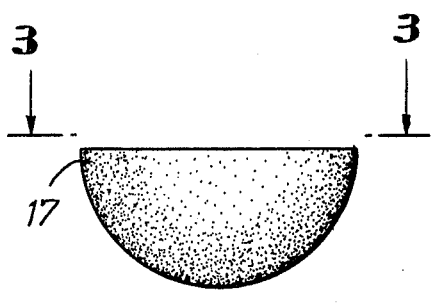
FIG. 1 is a side elevation of a dosage form embodied in the present invention.
Figure 2:
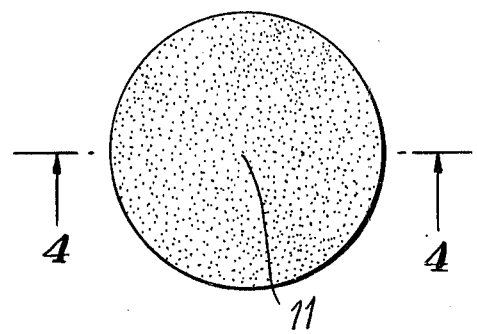
FIG. 2 is a top elevation of the dosage form shown in FIG. 1.
Figure 4:
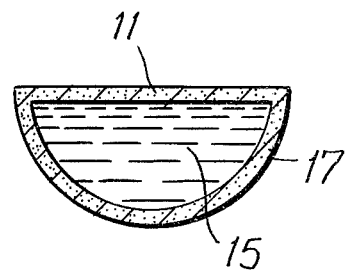
FIG. 4 is a cross-sectional view taken along line 2—2' of FIG. 2.

The product resulting from the above described process is shown in FIGS. 1, 2 and 4. The shell body is shown at 17 in FIG. 1; whereas, the cap of the product is shown at 11. The liquid center is shown at 15 in FIG. 4.

The following Examples are given to further illustrate the present invention. It is understood, however, that these are given by way of exemplification of this invention and that the invention is not limited thereto.

EXAMPLE 1

The following is a description of a method of manufacturing a sore throat cream in a liquid center product. The center is formulated as an anhydrous system.

| Shell | % by Weight |
|---|---|
| Mannitol | 90.00 |
| Glycerin | 10.00 |
| | 100.00 |

| Seal | % by Weight |
|---|---|
| Mannitol | 80.00 |
| Sorbitol, powder | 20.00 |
| | 100.00 |

| Cream Center | % by Weight |
|---|---|
| Propylene glycol dicaprylate/dicaprate (Neobee M-20) | 45.0 |
| Benzocaine | 2.0 |
| Sugar, 10X grade | 48.0 |
| Flavor Oil | 0.7 |
| Oil of Thyme | 0.1 |
| Eucalyptus Oil | 0.2 |
| Carrageenan Gum TP-4 (Marine Colloid) | 4.0 |
| | 100.0 |

Procedure:
Shell
1. Place a mixture of 90% mannitol and 10% anhydrous glycerin in an appropriate container fitted with a low RPM mixer.
2. Heat to 170°–175° C. and mix till uniform.
3. Cast into molds (2.5 ml capacity, hemispherical shape) until cavities are brim-full, hold for 3 seconds, invert to empty the excess molten material, and allow mold to cool to 15°–30° C. to crystalline and form the shell.

Cream Center
1. Heat the propylene glycol dicaprylate/dicaprate (Neobee M-20) to 10°–16° C. (50°–60° F.).
2. Add and dissolve the benzocaine with mixing.
3. Add the flavor oil, oil of thyme, and eucalyptus oil, and mix.
4. Add the carrageenan and mix until dispersion is uniform.
5. Add the sugar and mix until dispersion is uniform.
Note: Cream center may be safely stored for limited time (60 days) at room temperature in clean, well-closed containers. Remix before use.

Filling
Fill 2 gm of cream center into each shell, vibrating if necessary to eliminate air bubbles and produce a smooth surface.

Seal
Melt a mixture of 80% mannitol and 20% powdered sorbitol at 160°–170° C. Mix until uniform. Seal the top of the filled shell to the brim of the mold with this material, and allow to cool.

EXAMPLE 2

Sore throat cream with water-in-oil emulsion as liquid center

Shell

|  | % by Weight |
| --- | --- |
| Mannitol | 90.00 |
| Glycerin | 10.00 |
|  | 100.00 |

Seal
Carbowax 6000 (CTFA name PEG-150)
Cream Center (Water-in-oil emulsion)

|  | % by Weight |
| --- | --- |
| Benzocaine | 2.00 |
| Lecithin B70L (Cleary Corporation) | 10.00 |
| Coconut Oil Triglyceride, (Neobee M-5) | 30.00 |
| Insoluble Saccharin | 0.30 |
| Cherry flavor | 0.50 |
| Sorbitol 70% solution | 57.20 |
|  | 100.00 |

Procedure:
Shell
1. Place a mixture of 90% mannitol and 10% anhydrous glycerin in an appropriate container fitted with a low RPM mixer.
2. Heat to 170°–175° C. and mix till uniform.
3. Cast into molds (2.5 ml capacity, hemispherical shape) until cavities are brim full, hold for 3 seconds, invert to empty the excess molten material, and allow mold to cool to 25°–35° C. to crystallize and form the shell.

Cream Center (Water-in-Oil Emulsion)
1. Warm the benzocaine, lecithin and saccharin in the Neobee M-5 till dissolved.
2. Cool to 25° C.
3. Add the Sorbitol 70% solution to the oil phase with high speed stirring.
4. Add the flavor oil.

Filling
Fill 2 gm of cream center into each shell, vibrating if necessary to eliminate air bubbles and produce a smooth surface.

Seal
1. Heat the Carbowax 6000 to 75° C. till melted and uniform.
2. Seal the top of the filled shell to the brim of the mold with this material and cool to 35° C.

EXAMPLE 3

Cold and Cough Product

The shell and seal are the same system as used in Example 1 as well as the procedure for making and filling.

Liquid Center Gel

|  | % by Weight |
| --- | --- |
| Propylene glycol dicaprylate/ dicaprate (Neobee M-20) | 45.00 |
| Dextromethorphan HBr | 0.50 |
| d-Pseudoephedrine HCl | 2.00 |
| Sugar 10X grade | 49.50 |
| Flavor Oil | 0.70 |
| Oil of Thyme | 0.10 |
| Oil of Eucalyptus | 0.20 |
| Viscarin Carrageenan Gum | |

|  | % by Weight |
| --- | --- |
| #402 (Marine Colloid) | 2.00 |
|  | 100.00 |

EXAMPLE 4

Antacid Emulsion

The shell and seal are the same system as used in Example 1 as well as the procedure for making and filling.

Antacid Emulsion (Water-in-Oil Type)

|  | % by Weight |
| --- | --- |
| Mineral Oil 55/65 | 10.00 |
| Arlacel 186 | 1.00 |
| Propylparaben | 0.05 |
| Flavor #132 (Felton Inc.) | 0.10 |
| Sorbitol 70% Solution | 34.00 |
| Sodium Saccharin | 0.20 |
| Water | 40.55 |
| Calcium carbonate | 6.00 |
| Magnesium hydroxide | 2.00 |
| Methylparaben | 0.10 |
| Sugar Bakers Special | 6.00 |
|  | 100.00 |

Procedure:

Homogenize the mineral oil, Arlacel 186, flavor oil and Sorbitol 70% solution until a thick gel forms. To the water add propylparaben, methylparaben, sodium saccharin, sugar, calcium carbonate, magnesium hydroxide and disperse using high speed mixing. Slowly add the water phase to the oil phase while mixing. Homogenize the entire batch.

Although the invention has been described with reference to specific forms thereof, it will be understood that many changes and modifications may be made without departing from the spirit of this invention.

What is claimed is:

1. An edible unit dosage form capable of delivering a liquid or soft gel product comprising:
    (a) an outer relatively hard edible shell made of meltable material which is moldable by slush molding techniques and removable from the mold without residual tack, comprising from about 80% to about 100% by weight based on the total weight of the shell material of mannitol; and
    (b) a liquid or gel center contained within said shell said liquid or gel center comprising an oil base or water-in-oil emulsion base containing a pharmaceutically effective amount of medicament, said shell being sealed to the atmosphere with sealing material to contain said liquid or gel center within said shell.

2. A process for preparing an edible unit dosage form comprising an outer edible shell and a liquid or soft gel center which comprises:
    (a) forming a melt containing at least 50% by weight of mannitol;
    (b) pouring said melt into a mold cavity to substantially fill the same with said melt;
    (c) permitting said melt to cool sufficiently to form a shell having an opening therein;
    (d) removing the excess molten material;

(e) introducing into said formed shell a liquid or gel product to a level adjacent the upper margin of said shell;

(f) forming a melt of sealing material;

(g) introducing said sealing material into said liquid or gel product;

(h) allowing said sealing material to solidify whereby a sealing means is formed which seals off the liquid or gel contents of the shell from the outer atmosphere.

3. A unit dosage form according to claim 1 in which said shell material also includes a material selected from the group consisting of sorbitol, glycerin, propylene glycol, sugar and mixtures thereof.

4. A unit dosage form according to claim 1 in which said sealing material comprises a material which in molten condition is floatable on said liquid or gel center.

5. A unit dosage from according to claim 4 in which said sealing material is selected from the group consisting of mannitol, sorbitol, polyethylene glycol of formula $H(OCH_2CH_2)_nOH$ where n has an average value of 75, polyethylene glycol of formula $H(OCH_2CH_2)_{n'}OH$ where n' has an average value of 150 and mixtures thereof.

6. A unit dosage form according to claim 5 in which said sealing material also includes a material selected from the group consisting of glycerin, propylene glycol, butylene glycol, sugar, medicaments, flavors, colorants and mixtures thereof.

7. A unit dosage form according to claim 1 wherein the pharmaceutically effective amount of medicament contained in said liquid or gel center is selected from the group consisting of antiseptics, topical anesthetics, pulmonary decongestants, cough suppressants, analgesics, anti-pyretics, antihistamines, antacids and mixtures thereof.

8. An edible sore throat remedy in unit dosage form comprising:

(a) an outer relatively hard edible shell made of meltable material which is moldable by slush molding techniques and removable from the mold without residual tack, comprising from about 80% to about 100% by weight of mannitol; and (b) an anhydrous liquid center containing a therapeutically effective amount of a material selected from the group consisting of benzocaine, hexylresorcinol and mixtures thereof;

(c) said shell being sealed from the atmosphere with a sealing material selected from the group consisting of polyethylene glycol of formula $H(OCH_2CH_2)_nOH$ where n has an average value of 75, polyethylene glycol of formula $H(OCH_2CH_2)_{n'}OH$ where n' has an average value of 150, mannitol, sorbitol and mixtures thereof.

9. A unit dosage form according to claim 8 in which said sealing material is a mixture of mannitol and sorbitol.

10. An edible sore throat remedy in unit dosage form comprising:

(a) an outer relatively hard edible shell made of meltable material which is moldable by slush molding techniques and removable from the mold without residual tack, comprising from about 80% to about 100% by weight of mannitol; and (b) a water-in-oil emulsion liquid center containing a therapeutically effective amount of benzocaine, hexylresorcinol and mixtures thereof;

(c) said shell being sealed from the atmosphere with a sealing material selected from the group consisting of polyethylene glycol of formula $H(OCH_2CH_2)_nOH$ where n has an average value of 75, polyethylene glycol of formula $H(OCH_2CH_2)_{n'}OH$ where n' has an average value of 150, mannitol, sorbitol and mixtures thereof.

11. A unit dosage form according to claim 10 wherein said sealing material is polyethylene glycol of formula $H(OCH_2CH_2)_{n'}OH$ where n' has an average value of 150.

12. An edible cough and cold product in unit dosage form comprising:

(a) an outer relatively hard edible shell made of meltable material which is moldable by slush molding techniques and removable from the mold without residual tack, comprising from about 80% to about 100% by weight of mannitol; and (b) a liquid center gel containing a therapeutically effective amount of a material selected from the group consisting of dextromethorphan and its salts, d-pseudoephedrine and its salts, and mixtures thereof;

(c) said shell being sealed from the atmosphere with a sealing material selected from the group consisting of polyethylene glycol of formula $H(OCH_2CH_2)_nOH$ where n has an average value of 75, polyethylene glycol of formula $H(OCH_2CH_2)_{n'}OH$ where n' has an average value of 150, mannitol, sorbitol and mixtures thereof.

13. A unit dosage form according to claim 12 in which the therapeutically active material contained in said liquid center gel contains a mixture of dextromethophan HBr and d-pseudoephedrine HCl.

14. An edible antacid product in unit dosage form comprising:

(a) an outer relatively hard edible shell made of meltable material which is moldable by slush molding techniques and removable from the mold without residual tack, comprising from about 80% to about 100% by weight of mannitol; and (b) a water-in-oil antacid emulsion liquid center containing a therapeutically effective amount of an antacid selected from the group consisting of calcium carbonate, magnesium hydroxide, aluminum hydroxide and mixtures thereof;

(c) said shell being sealed from the atmosphere with a sealing material selected from the group consisting of polyethylene glycol of formula $H(OCH_2CH_2)_nOH$ where n has an average value of 75, polyethylene glycol of formula $H(OCH_2CH_2)_{n'}OH$ where n' has an average value of 150, mannitol, sorbitol and mixtures thereof.

15. A unit dosage form according to claim 14 in which the antacid is a mixture of calcium carbonate and magnesium hydroxide.

16. An edible analgesic product in unit dosage form comprising:

(a) an outer relatively hard edible shell made of meltable material which is moldable by slush molding techniques and removable from the mold without residual tack, comprising from about 80% to about 100% by weight of mannitol; and (b) a liquid or gel center comprising an oil base or a water-in-oil emulsion base containing a therapeutically effective amount of an analgesic selected from the group consisting of aspirin, acetaminophen and mixtures thereof;

(c) said shell being sealed from the atmosphere with a sealing material selected from the group consisting of polyethylene glycol of formula H(OCH$_2$CH$_2$)$_n$OH where n has an average value of 75, polyethylene glycol of formula H(OCH$_2$CH$_2$)$_{n'}$OH where n' has an average value of 150, mannitol, sorbitol and mixtures thereof.

17. An edible cold product in unit dosage form comprising:

(a) an outer relatively hard edible shell made of meltable material which is moldable by slush molding techniques and removable from the mold without residual tack, comprising from about 80% to about 100% by weight of mannitol; and (b) a liquid or gel center comprising an oil base or a water-in-oil emulsion base containing a therapeutically effective amount of a mixture of acetaminophen and phenylpropanolamine hydrochloride;

(c) said shell being sealed from the atmosphere with a sealing material selected from the group consisting of polyethylene glycol of formula H(OCH$_2$CH$_2$)$_n$OH where n has an average value of 75, polyethylene glycol of formula H(OCH$_2$CH$_2$)$_{n'}$OH where n' has an average value of 150, mannitol, sorbitol and mixtures thereof.

18. A dosage form according to claims 1, 8, 10, 12, 14, 16 or 17 in which the edible shell contains 90% by weight of mannitol and 10% by weight of glycerin.

* * * * *

UNITED STATES PATENT AND TRADEMARK OFFICE
CERTIFICATE OF CORRECTION

PATENT NO. : 4,260,596
DATED : April 7, 1981
INVENTOR(S) : Leonard Mackles

It is certified that error appears in the above-identified patent and that said Letters Patent are hereby corrected as shown below:

Claim 1, line 3, change "relatingly" to -- relatively --

Claim 1, Claim 8, Claim 10, Claim 12, Claim 14, Claim 16 and Claim 17 after "mannitol" and before the (;) insert -- or mixtures thereof with glycerin, sorbitol, propylene glycol, colorants, sugars or medicaments --

Signed and Sealed this

Twenty-first Day of July 1981

[SEAL]

Attest:

Attesting Officer

GERALD J. MOSSINGHOFF

Commissioner of Patents and Trademarks